United States Patent [19]

Pocock

[11] 4,124,301
[45] Nov. 7, 1978

[54] DEVICE FOR MEASURING LIGHT TRANSMITTED THROUGH A MATERIAL

[75] Inventor: Sydney N. Pocock, Carshalton, England

[73] Assignee: National Research Development Corporation, London, England

[21] Appl. No.: 738,172

[22] Filed: Nov. 2, 1976

[30] Foreign Application Priority Data

Nov. 5, 1975 [GB] United Kingdom ............... 45918/75

[51] Int. Cl.² .............................................. G01N 21/24
[52] U.S. Cl. ................................... 356/432; 250/573; 356/434; 356/442
[58] Field of Search ............... 356/201, 204, 205, 206, 356/208; 250/573

[56] References Cited

U.S. PATENT DOCUMENTS

| | | | |
|---|---|---|---|
| 3,437,822 | 4/1969 | Fitzsimmons | 356/205 |
| 3,463,927 | 8/1969 | Allington | 356/206 |
| 3,489,906 | 1/1970 | Beer | 356/208 |
| 3,528,749 | 9/1970 | Bowker | 356/206 |
| 3,901,600 | 8/1975 | Johnson et al. | 356/205 |
| 4,003,662 | 1/1977 | Retzer et al. | 356/206 |

FOREIGN PATENT DOCUMENTS 1,240,294  5/1967  Fed. Rep. of Germany.
2,003,449  7/1971  Fed. Rep. of Germany.
1,773,227  8/1974  Fed. Rep. of Germany.

Primary Examiner—John K. Corbin
Assistant Examiner—R. A. Rosenberger
Attorney, Agent, or Firm—Cushman, Darby & Cushman

[57] ABSTRACT

In a device for measuring the transmitting or absorbing properties of a material at ultra-violet, visible or infra-red frequencies, the light source is operated in a flash mode, a signal is derived related to the light from the source received by a detector after passing through the material, and a biased manual switch is connected so that a display related to the derived signal is provided only while the switch is held closed. When the light source used is an incandescent lamp, a temperature sensor is provided to activate the processing and display circuitry when the filament lamp reaches a predetermined operating temperature.

5 Claims, 10 Drawing Figures

DEVICE FOR MEASURING LIGHT TRANSMITTED THROUGH A MATERIAL

This invention relates to devices for measuring the light transmitted through a material, which may be a fluid or a solid. In this specification the term "light" is intended to include visible, ultra-violet and infra-red radiation A problem frequently encountered with battery operated measuring devices is that if they are left switched on when not in actual use, the current drawn may deplete the battery very quickly. In both battery and mains operated measuring instruments other components such as light sources may also need to be replaced frequently, and the problem may be acute in developing countries. Furthermore, many measuring instruments have a considerable "warm-up" period during which reliable measurements cannot be obtained. The object of this invention is to maximise component life and substantially eliminate the warm-up period of a device for measuring light transmittance or absorbance, and also to provide a device which is simple to use.

According to the invention a device for measuring the light transmitted through a material comprises a light source; a light detector spaced from the source; circuit means arranged to operate the source in a flash mode and to derive a signal in accordance with the intensity of light received from the light source by the detector; display means connected to the circuit means so as to provide a display related to the derived signal; and a manually operable switch arranged to initiate operation of the circuit means and to maintain the displayed reading while the switch is operated.

In one type of device according to the invention, the circuit means is arranged to derive a reference signal in accordance with the intensity of light received from the source by a light detector after transmission through a reference material, and to derive a sample signal in accordance with the intensity of light received from the source by a light detector after transmission through a material under test, the circuit means further comprising timing means to determine the time taken for an exponential decay from the greater to the lesser of the reference signal and the sample signal, and the derived signal being related to the decay time.

The light source may be, for example, a light emitting diode (LED), or may be a source of white light, optionally in conjunction with at least one colour filter or monochromator. Alternatively the source may be a lamp filament such as a tungsten lamp, the circuit means then further comprising means to detect the attainment by the lamp filament of a predetermined operating temperature, and to cause the signal in accordance with the intensity of light received by the detector to be derived after that temperature has been reached.

The derived signal may be the instantaneous output or the maximum output or the integral of the output of the light detector.

There may also be further provided circuit means arranged to operate the source to provide a series of flashes, the display means then providing while the manual switch is operated a display related to a signal derived in accordance with the intensity of light received by a detector during the immediately preceding flash.

The invention will now be described by way of example with reference to the accompanying drawings in which:-

FIG. 1 illustrates a device according to the invention in block diagram form in which an analogue signal is displayed;

FIGS. 2(a) and 2(b) illustrate two alternative sequences of operation of the components of a device having a LED source;

In FIGS. 2(a), 2(b), 4, 6(b) and 7, the abcissae indicating passage of time are not to scale.

Figure 1:
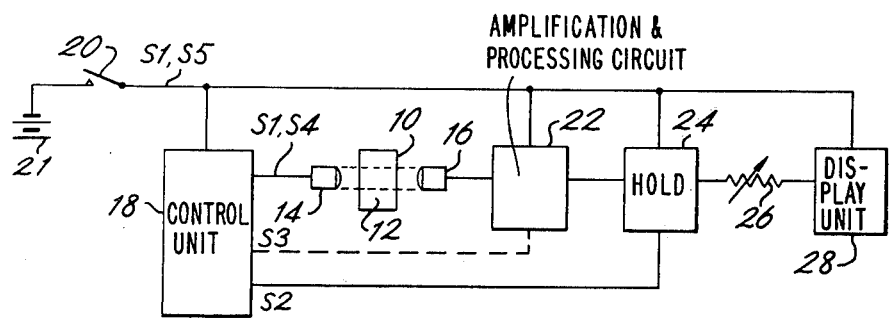

In FIG. 1, a cuvette 10 containing a liquid sample 12 is placed between a LED 14 and a photodiode detector 16. The LED is connected through a control circuit 18 to a first side of a reed switch 20 which is biased into the open position. The second side of the switch 20 is shown connected to a battery 21, but alternatively a mains supply could be used.

The photodiode 16 is connected through an amplification and processing circuit 22 to a 'hold' device 24, which is connected through a variable resistor 26 to a display unit 28. The circuit 22, hold device 24 and display unit 28 are all connected to the first side of switch 20, and the circuit 22 is also connected to the control circuit 18. The power return line is not shown.

The sequence of operation will now be described with reference to FIGS. 1 and 2(a). No power is drawn from the battery until the switch 20 is manually closed against the bias and is held in that position. Closing the switch provides a signal S1 which causes power to be supplied through the control circuit 18 to the LED 14, which rapidly reaches a stable output of monochromatic light, as indicated by curve A. The photodiode 16 reaches a stable output, corresponding to the light transmitted through the liquid 12 and cuvette 10, at a rather slower rate, as shown by curve B. The signal S1 also causes the amplification and processing circuit 22 to be energised as shown by curve D; the circuit may, for example, convert the photodiode output to a signal representing the transmittance or absorbance of the liquid 12. After a predetermined time, long enough to allow transients to have subsided and for the photodiode output to have reached a stable level, the control circuit 18 produces a signal S2 which causes the instantaneous signal provided by circuit 22 to be connected to the hold device 24 which supplies the signal through variable resistor 26 to the display unit 28. The operation of the display unit is represented by curve C; the hold device 24 supplies a constant signal, which is displayed by display unit 28 as long as unit 18 is energised through switch 20.

Shortly after the signal S2, the control circuit 18 produces a signal S4 which cuts off power from the LED as shown by curve A; the time between signals S1 and S4 may be of the order of milliseconds. The photodiode ceases to give an output, as shown by curve B. After the display on unit 28 has been noted by an observer, the switch 20 is allowed to open, all power is disconnected from the device and all components including the display unit cease to operate.

The device therefore draws current from the battery 21 only when an operator holds switch 20 in the closed position against the bias; the device cannot be left "switched on", and power consumption is minimised because the LED operates only between signals S1 and S4 e.g. the LED draws about 50 milliamps for a few milliseconds. After that time, only hold device 24 and display unit 28 are operating and power consumption is very low. The amplification and processing current 22 is energized between signals S1 and S5, but the photodiode 16 does not provide an output signal for the circuit to process after signal S4 has cut off the LED. The duration of operation of the LED is short enough to prevent heating of any other parts of the device, and it has been found that reproducible results can be obtained without the normal "warm-up" period which is necessary with conventional devices.

Figure 2A:
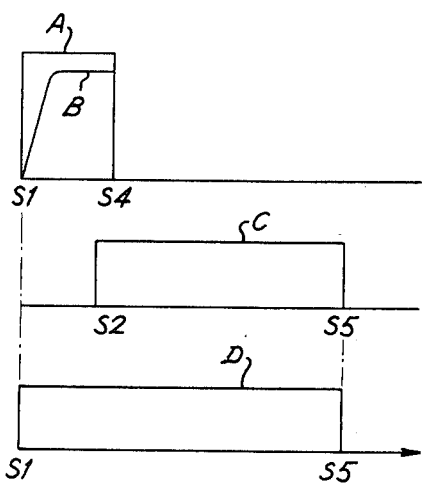
Figure 2B:
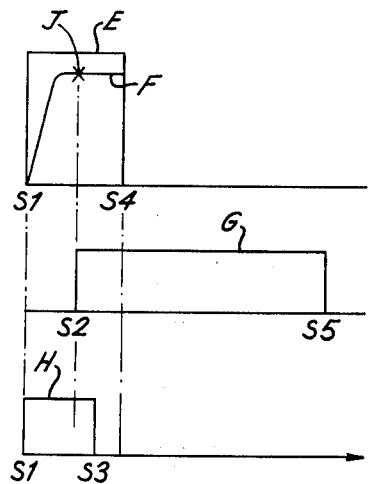
Figure 3:
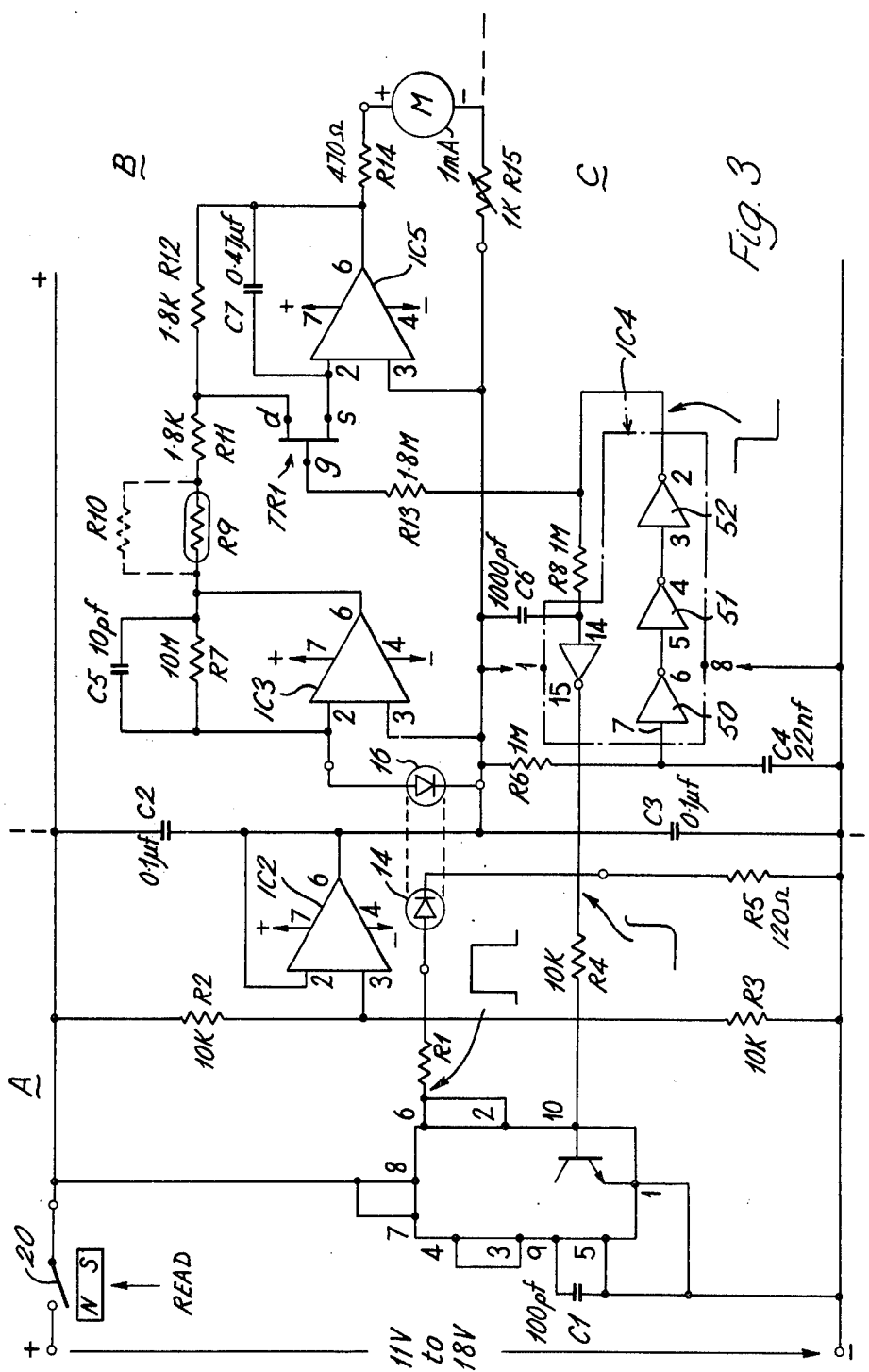
FIG. 3 illustrates an electronic circuit for operation of the device in the sequence shown in FIG. 2(a)

A full circuit diagram corresponding to FIG. 2 is shown in FIG. 3 which can be considered in three parts. The left hand portion A concerns the power supply and the pulse drive to the LED light source 14. The top right hand portion B includes the photo-detector, the analogue circuits and memory, while the lower right hand portion C consists of a time-sequence generator which controls the internal sequence from the moment when the "press to read" switch 20 is operated.

Most of the circuits are powered from the unstabilised ± rails. Between these an electronic centre-tap is derived by IC2 (a type 307) referenced by the junction point of equal resistors R2, and R3. This centre rail is designated 0v and is the main reference point for all the analogue circuits. The decoupling capacitors C2, C3 shunt two halves of the power supply. The "press to read" switch 20 must have a contact bounce time limited to a few milliseconds and a sealed magnetically operated switch may be used for climatic durability. The stablising circuit IC1 (a type μA 723C) is used only to pulse the light emitting diode 14 with 7V applied through the current limiting resistors R1, R5, (R1 being used to set the maximum current and R5 being selected on test if necessary to take up brightness tolerance in LED 14). The control pin 10 of IC1 normally used for overload protection is utilised for terminating the 7v pulse to the LED circuit. Capacitor C1 is necessary for stability reasons.

Green light at approximately 567 nanometres is emitted by LED 14 and transmitted through the cuvette 10 (see FIG. 1) to the silicon diode 16 which, in the unbiased mode, may be regarded as a current source. This produces a proportional voltage at the output pin 6 of IC3 (a type 536); the feed-back circuit consists of the 10MΩ resistor R7 shunted by the stabilising capacitor of 10 pF designated C5. The output voltage (proportional to the light transmitted through the cuvette) is applied to a "see-saw" "follow and hold" circuit, comprising equal resistors R11, R12 and the FET amplifier IC5 (a type 536). Additional components associated with this are the FET follow/hold switch TR1, and the analogue storage capacitor C7 of value 0.47μF. Neglecting for the moment the thermistor R9 the application of a negative voltage from IC3 will produce an equal positive output at pin 6 of IC5 while TR1 is closed and the whole circuit is "following". Before the end of the LED light pulse, TR1 goes open circuited into the "hold" mode. The output voltage of IC5 is indicated by the moving coil of meter M; the potentiometer R15 enables this to be set to 100% transmission, resistor R14 merely limiting the range of adjustment. The time-constant of acquisition when in the full mode is determined by the changing source resistance of the memory circuit which is approximately 1 kilohm and the capacitor C7. For the circuit to reach within 0.1% of the equilibrium value, a period of five times its time constant CR should be allowed after any initial transients, such as contact bounce of switch 20, have subsided; this is the time lag $S_1$ to $S_2$.

The resistor R11 may be reduced in value when an optional thermistor R9 is introduced in thermal contact with the cuvette/opto-electronic assembly. Resistor R10 also provides a means of proportioning the relative effect of the thermistor so as to cancel the overall temperature co-efficient over the desired range of ambient temperature, i.e. the see-saw circuit gain normal 1:1 ratio is varied by a limited percentage.

It remains to describe the timing function generator which consists of IC4 and associated components. IC4 (a type MC 14049) is a hex-inverter leaving two unused sections. When the supply is applied by the closure of switch 20, capacitor C4 will hold the input for the first inverter 50 fully negative, but it will begin to charge exponentially. When the hex-inverter transition voltage (which is very approximately 40% of that half of the supply voltage) is reached, pin 6 will swing negatively. This transition however is not very fast and two further inverter sections 51, 52 are used to give a really rapid voltage transition from pin 2 of inverter 52 which provides the negative going 'hold' command applied through resistor R13 to the FET switch TR1. The flash of the LED 14 can now be terminated as the optical measurement has been completed and the related value is 'held'. To obviate any danger of the LED light beginning to decay before the "hold" instruction is complete, a further short time-delay (very non-critical) is obtained by R8, C6 and the fourth section of IC4. The positive going drive from pin 15 of IC4 is applied via R4 to drive pin 10 of IC1 positive to inhibit the 7v pulse output a pin 6 which drives the LED. The "hold" command is approximately at 10 milliseconds and the additional delay approximately half a millisecond.

The use of integrated circuits with high supply rejection ratios with all vital functions referenced to the derived OV line allows the accuracy of the device to be substantially independent of supply variations between 11 and 18 volts.

It was stated during description of the mode of operation illustrated by FIG. 2(a) that the amplification and processing circuit 22 was energised throughout the operation of the device between signals S1 and S5. An alternative sequence of operation of the components is shown in FIG. 2(b). Closure of switch 20 produces a signal S1 which energises the LED (curve E) and the amplification circuit 22 (curve H). The photodiode provides an output indicated by curve F. After a time long enough for the photodiode output to have stabilised as indicated by point J, the control circuit 18 provides a signal S2 which initiates operation of the hold device 24 and display unit 28 (curve G). The control circuit then produces a signal S3 which inhibits the supply of power to the amplification and supply circuit 22 as indicated by the dotted connection in FIG. 1. The control circuit then supplies signal S4 to terminate operation of the LED. This arrangement provides a further reduction of power consumption, but requires extra components.

Figure 4:
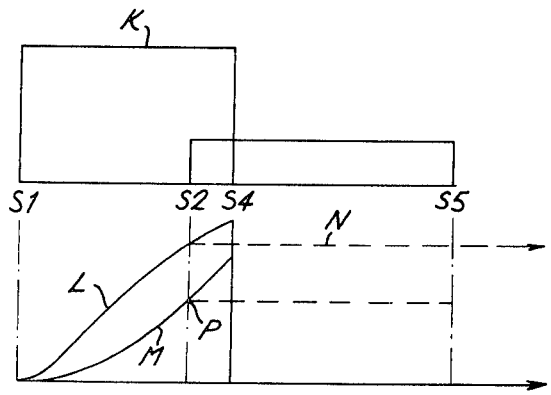
FIG. 4 illustrates the sequence of operation of a device having a filament lamp source.

FIG. 4 illustrates the mode of operation when the LED 14 in FIG. 1 is replaced by a lamp filament, such as a tungsten lamp. The lamp is operated in a flash mode between the times of signals S1 and S4 as shown by curve K, but the temperature, and therefore the brightness, of the lamp increases with time as shown by curve L. The output of the photodiode 16 increases similarly after a time delay and is represented by curve M. The lamp temperature may be detected, for example, by a temperature or brightness sensor (not shown), and is compared by a comparator (not shown) with a stored signal represented by line N corresponding to required brightness. When the required level is reached, typically after less than 1 second, the comparator causes the signal at time S2 to be provided, and the hold device supplies to display unit 28 a signal corresponding to point P on curve M. The output from the photodiode is therefore always sampled at the same colour temperature. The lamp is not monochromatic and if required one or more filters or monochromators may be placed in the optical path.

Figure 5:
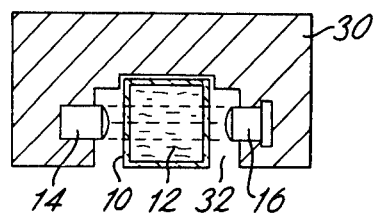
FIG. 5 illustrates one arrangement of a LED source, sample fluid cuvette and detector for a single flash, single beam device.

FIG. 5 shows the arrangement of source, sample and detector for the device illustrated in FIGS. 1 and 2. The LED 14 and photodiode 16 are encapsulated in an epoxy resin block 20 which has a recess 32 in which the cuvette 10 of liquid 12 can be placed. The device provides a single flash and a single beam of light for each sample, and must be calibrated before use to provide a scale which displays, for example, percentage transmission or absorption.

Between samples, it is normal practice to check the zero setting of a measuring instrument in the absence of a sample. Conveniently, zero absorbance, or 100% transmission, is set by means such as a variable iris diaphragm in the optical path, or by a variable gain amplifier connected to the photocell. With a flash operated instrument, setting the absorbance reading to zero in such a way would require a tedious trial and error sequence of repeated flashes. In the instrument according to the invention, by holding the display unit 'on' with switch 20 and altering resistor 26 which in effect alters amplification or instrument sensitivity, the held reading can be set to zero using only one flash.

Figure 6A:
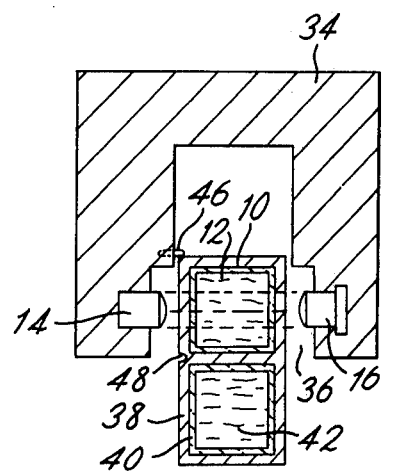
FIG. 6(a) illustrates an arrangement of a LED source, sample and reference fluid cuvettes, and detector for a double flash, single beam device.
Figure 6B:
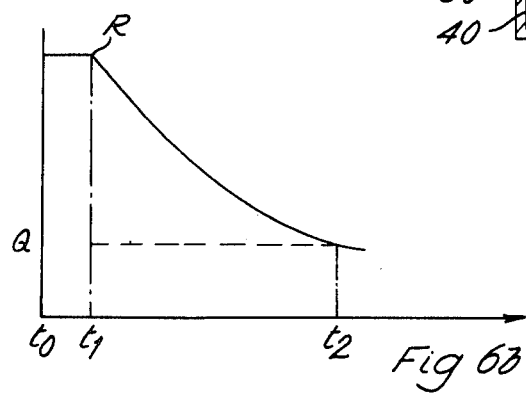
FIG. 6(b) illustrates the provision of an absorbance measurement in digital form.

An example of an arrangement of source, detector and sample for a double flash device is shown in FIG. 6(a). The LED 14 and photodiode 16 are encapsulated in an epoxy resin block 34 having an aperture 36 which is slightly larger than a cuvette holder 38 which carries the cuvette 10 containing sample liquid 12 and also a reference cuvette 40, either containing a reference liquid 42, such as distilled water, or a reagent solution. The aperture 36 contains an indexing device 46 which co-operates with the leading edge of the cuvette holder, as shown, and also with a recess 48 in the cuvette holder; the indexing device 46 detects the two positions of the cuvette holder corresponding to the sample liquid 12 and the reference liquid 42 being consecutively in position between the source and the detector, and causes the timing circuit 18 (FIG. 1) to cause the LED to flash twice. The photodiode output consists of two signals, as shown in FIG. 6(b), signal Q corresponding to the sample liquid and signal R to the reference liquid. The amplification and processing circuit (22 in FIG. 1) is arranged to measure the time taken $(t_2 - t_1)$ for the signal at the reference level to decay exponentially to the sample signal level. This corresponds to an application of Beer's law, and allows absorbance, which is on a logarithmic scale, to be displayed by a linear device.

Figure 7:
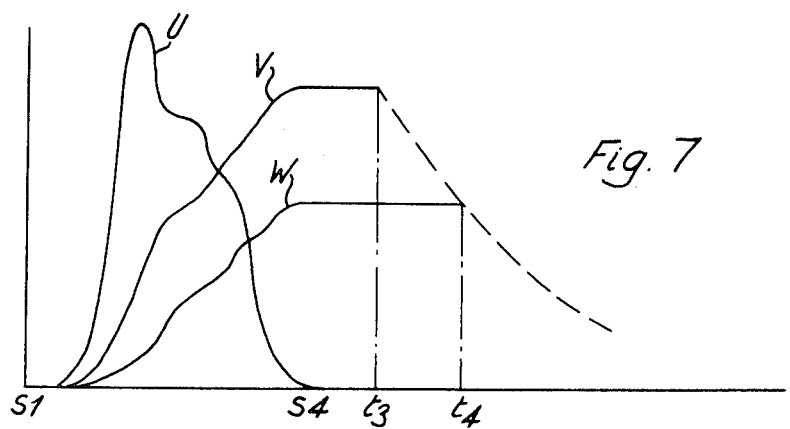
FIG. 7 illustrates the sequence of operation of a device having a gas-filled tube as a light source.
Figure 8:
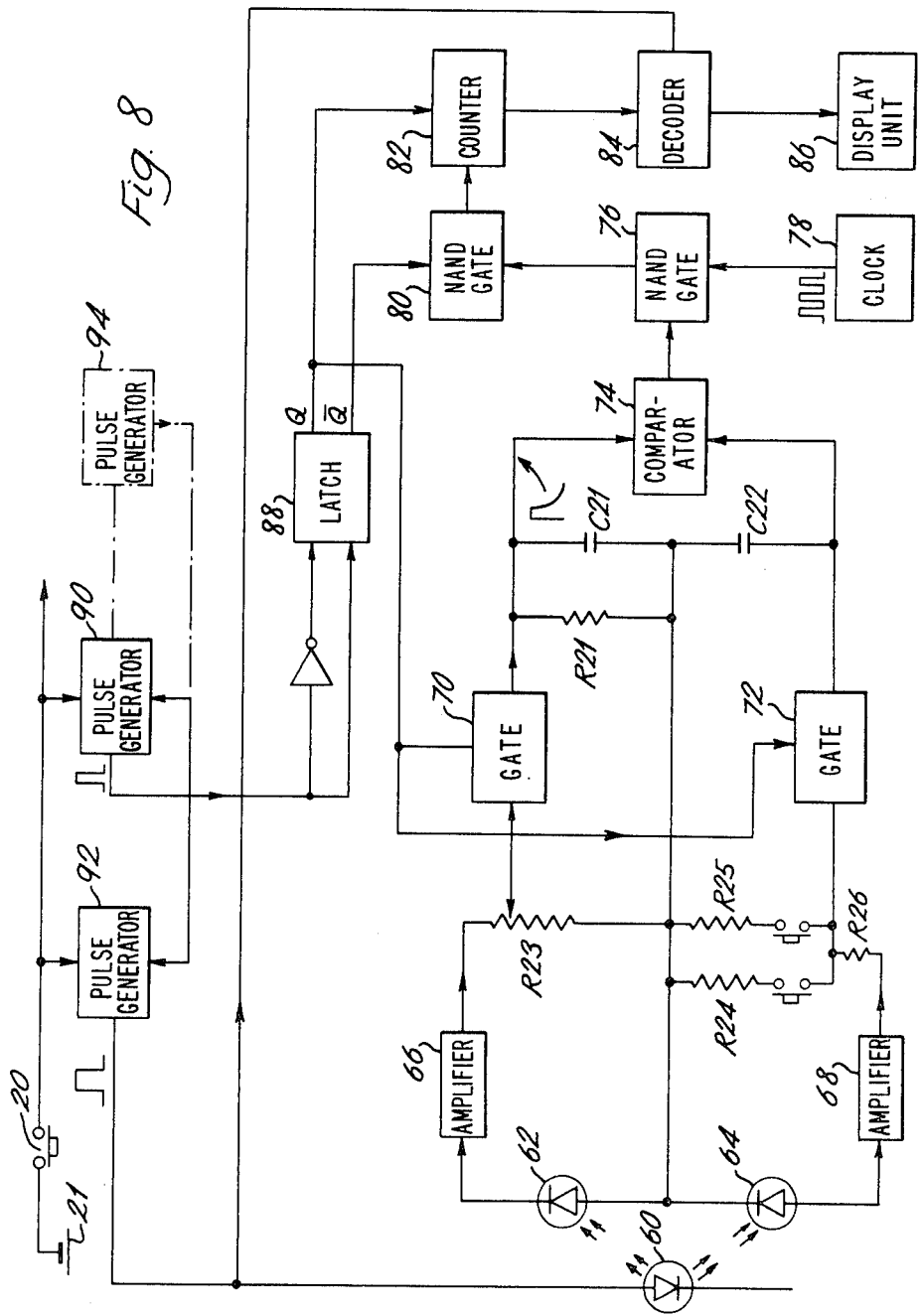
FIG. 8 illustrates a device according to the invention in block diagram form in which a digital signal is displayed.

Yet another mode of operation is illustrated by FIG. 7. In this example the source comprises, for example, a gas-filled tube such as a photographic flash tube, which does not provide an accurately reproducible light output. In this arrangement a single flash is used and two identical detectors are arranged to receive light transmitted through identical cuvettes containing respectively the sample liquid and a reference liquid. Such an arrangement of components is well known in the field of measurement of absorbance or transmittance of light and is not illustrated. In FIG. 7, the output of the flash tube is illustrated by the curve U; the envelope is irregular and it is therefore convenient to arrange the amplification and processing circuits associated with each detector to integrate the respective detector outputs, and the signals are represented by curves V and W, which each reach a plateau when integration is complete. The processing circuit then measures the time taken for an exponential decay represented by the chain-dotted line from one plateau to the other $(t_4 - t_3)$, the time representing, as before, the absorbance of the sample liquid, which is displayed by the display unit. A circuit suitable for making a time measurement is shown in FIG. 8. The circuit also provides a digital readout.

The LED source 60 is arranged to illuminate two photocells 62, 64 with a single flash of nominal length 14 milliseconds; photocell 62 is a reference photocell, is illuminated directly and may conveniently be cemented to the side of the source; photocell 64 is a sample photocell which receives light after passage through a material under test. The photocells are connected through respective amplifiers 66, 68 and transmission gates 70, 72 to two sample and hold circuits connected to a comparator 74 such as a type LF355. It is assumed that the sample photocell receives less light than the reference photocell, therefore sample and hold circuit $R_{21}$, $C_{21}$ associated with the reference photocell is arranged to decay exponentially with a time constant of the order of tens of milliseconds. The time constant of the reference sample and hold circuit $C_{22}$ is theoretically infinite; in practice 10 seconds is sufficient.

After initiation of the LED flash at time $t_o$, (FIG. 6b) the outputs of amplifiers 66, 68 are connected to their respective sample and hold circuits for nominally 10 milliseconds. When the transmission gates 70, 72 are switched off at time $t_1$, the voltage across capacitor $C_{22}$ remains constant while that across $C_{21}$ decays until it equals the voltage on $C_{22}$; this equality is detected by the comparator 74 which provides an output signal at this time $t_2$, by changing between a high and a low output.

The time interval $t_1$ to $t_2$ is proportional to the absorbance of the test material, provided the outputs of amplifiers 66, 68 are first equalised by a calibration procedure using potentiometer $R_{23}$.

To measure the time interval, the comparator 74 is connected to a two-input NAND gate 76 which is supplied with pulses by a clock 78 and the output of which is connected to a second two-input NAND gate 80 which supplies a resettable counter 82, decoder 84 and digital display unit 86. The second input of NAND gate 80 is supplied through a pulse sharpening latch 88 which also controls the operation of the transmission gates 70, 72, from a 10 millisecond pulse generator 90. A 14 millisecond pulse generator 92 controls the LED 60 and both generators are connected through the manual switch 20 to a supply 21.

The comparator 74 causes clock pulses to be provided from NAND gate 76 between times $t_o$ and $t_2$ to the NAND gate 80. The gate 80 is supplied by pulse generator 90 through latch 88 with a replica of the switching pulses used to control transmission gates, i.e. between times $t_o$ and $t_1$. The arrangement is such that clock pulses appear at the output of NAND gate 80 only during the time interval $t_1$ to $t_2$ (typically less than 100 milliseconds). These pulses are counted by counter 82 and displayed digitally by display unit 86.

In some circumstances, for example, when a chemical reaction is taking place in the sample material, it may be desirable to provide a LED flash which is repeated at intervals, the digital display being updated with each flash. Any drift can then be detected by change in the displayed quantity. This can be achieved by providing an optional 1 second pulse generator 94 which restarts the operation of generators 90 and 92 at 1 second intervals. The LED then flashes at 1 second intervals, and the display is updated at 1 second intervals so long as switch 20 is held manually closed.

Since the majority of the current is consumed equally by the digital display unit 86 and the light source LED 60, it may be arranged that the display is electronically blanked out during operation of the light source LED 60 in order to reduce the maximum current demand where the consumption of the display unit is appreciable.

Choice of the values of $C_{21}$, $R_{21}$ and the frequency of the clock pulses allows a desired scaling factor to be chosen so that the display can provide a reading of, for example, optical density, i.e. absorbance, or of the haemoglobin content of a blood sample in grams per 100 milliliters. Calibration is checked by electrical simulation of absorbance at two points on the digital scale by push button attenuators $R_{24}$, $R_{25}$, in conjunction with resistor $R_{26}$ which must be large enough to swamp the tolerances on the output resistance of amplifier 68.

It is to be understood that some features of the device are interchangeable. For example, the repeated flash and updating can be used with an analogue display.

I claim:

1. A device for determining the light received from an illuminated material comprising: a filament lamp; a light detector spaced from the lamp; circuit means arranged to operate the filament lamp in a flash mode and to derive a signal in accordance with the intensity of light received from the filament lamp by the detector; temperature sensing means arranged to detect the attainment by the lamp filament of a predetermined operating temperature and to allow derivation of said signal only after that level has been reached; display means connected to the circuit means so as to provide a display related to the derived signal; and a normally open manually operable switch arranged so that only while the switch is closed: (a) operation of the circuit means is initiated and (b) a display is maintained.

2. A device according to claim 1 in which the circuit means is arranged to derive a reference signal in accordance with the intensity of light received by a light detector from a reference material illuminated by a flash of the filament lamp, and to derive a sample signal in accordance with the intensity of light received by a light detector from a material under test illuminated by a flash of the filament lamp; the circuit means further comprising timing means to determine the time taken for an exponential decay from the greater to the lesser of the reference signal and the sample signal, and the derived signal being related to the decay time.

3. A device according to claim 2 further comprising means to position a reference material and a material under test consecutively between the filament lamp and the light detector; and means for operating the filament lamp to illuminate each material with a flash of light.

4. A device according to claim 2 further comprising means to direct light from the filament lamp along two respective optical paths to two light detectors; and means to position a reference material and a material under test respectively in each optical path.

5. A device according to claim 1 in which there is further provided circuit means arranged to operate the filament lamp to provide a series of flashes, the display means then providing while the manual switch is operated a display related to a signal derived in accordance with the intensity of light received by a detector during the immediately preceding flash.

* * * * *